(12) United States Patent
Xiaohui et al.

(10) Patent No.: US 11,779,296 B2
(45) Date of Patent: Oct. 10, 2023

(54) PHOTON COUNTING DETECTOR BASED EDGE REFERENCE DETECTOR DESIGN AND CALIBRATION METHOD FOR SMALL PIXELATED PHOTON COUNTING CT APPARATUS

(71) Applicant: CANON MEDICAL SYSTEMS CORPORATION, Otawara (JP)

(72) Inventors: Zhan Xiaohui, Vernon Hill, IL (US); Qiang Yi, Vernon Hill, IL (US); Zhihong Ye, Vernon Hill, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 141 days.

(21) Appl. No.: 16/825,857

(22) Filed: Mar. 20, 2020

(65) Prior Publication Data

US 2021/0290195 A1 Sep. 23, 2021

(51) Int. Cl.
*A61B 6/03* (2006.01)
*A61B 6/00* (2006.01)
*G21K 1/02* (2006.01)

(52) U.S. Cl.
CPC ............ *A61B 6/5282* (2013.01); *A61B 6/032* (2013.01); *A61B 6/40* (2013.01); *A61B 6/4021* (2013.01); *A61B 6/42* (2013.01); *A61B 6/4208* (2013.01); *A61B 6/4233* (2013.01); *A61B 6/4241* (2013.01); *A61B 6/4266* (2013.01); *A61B 6/4275* (2013.01); *A61B 6/4291* (2013.01); *A61B 6/4435* (2013.01); *A61B 6/482* (2013.01); *A61B 6/483* (2013.01); *A61B 6/5258* (2013.01);

(Continued)

(58) Field of Classification Search
CPC ............ A61B 6/032; A61B 6/035; A61B 6/40; A61B 6/4021; A61B 6/42; A61B 6/4208; A61B 6/4233; A61B 6/4241; A61B 6/4266; A61B 6/4291; A61B 6/44; A61B 6/4429; A61B 6/4435; A61B 6/4441; A61B 6/4447; A61B 6/52; A61B 6/5258; A61B 6/5282; A61B 6/482; A61B 6/4275; A61B 6/483; A61B 6/582; G01N 23/046; G21K 1/02; G21K 1/025
USPC ........ 378/7, 19, 98.8, 147, 154, 207, 5, 149, 378/98.9; 250/370.09
See application file for complete search history.

(56) References Cited

U.S. PATENT DOCUMENTS 4,866,744 A * 9/1989 Yoshida ................. G21K 1/025
378/7
4,991,189 A * 2/1991 Boomgaarden .......... A61B 6/06
378/151

(Continued)

FOREIGN PATENT DOCUMENTS

CN 101002108 A 7/2007

*Primary Examiner* — Allen C. Ho
(74) *Attorney, Agent, or Firm* — Oblon, McClelland, Maier & Neustadt, L.L.P.

(57) ABSTRACT

An apparatus and a method for correcting for signal variations in pixels of a main photoelectric conversion element in a radiation detection apparatus due to focal spot position drifts. Edge reference detectors are positioned next to a main detector, in a fan beam coverage but outside a scan field of view. The signal variations of the edge reference detectors under an anti-scatter-grid shadow are used to estimate a real-time focal spot movement, which is used to estimate a shadow/signal variation on the main detector that are in the scan field of view.

16 Claims, 9 Drawing Sheets

(52) U.S. Cl.
CPC ............ *A61B 6/582* (2013.01); *G21K 1/02* (2013.01); *G21K 1/025* (2013.01)

(56) References Cited

U.S. PATENT DOCUMENTS

| | | | | |
|---|---|---|---|---|
| 4,995,107 | A * | 2/1991 | Klingenbeck | A61B 6/032 378/19 |
| 5,131,021 | A * | 7/1992 | Gard | G21K 1/025 378/146 |
| 5,291,402 | A * | 3/1994 | Pfoh | A61B 6/032 378/13 |
| 5,469,429 | A * | 11/1995 | Yamazaki | H01J 35/24 378/113 |
| 5,579,359 | A * | 11/1996 | Toth | A61B 6/032 378/19 |
| 5,583,903 | A * | 12/1996 | Saito | A61B 6/032 378/19 |
| 5,610,963 | A * | 3/1997 | Hsieh | G01T 1/29 378/151 |
| 5,684,855 | A * | 11/1997 | Aradate | A61B 6/032 378/145 |
| 5,949,843 | A * | 9/1999 | Tamaki | A61B 6/032 378/17 |
| 6,094,469 | A * | 7/2000 | Dobbs | A61B 6/4021 378/19 |
| 6,215,844 | B1 * | 4/2001 | Adachi | A61B 6/032 378/19 |
| 7,149,283 | B2 * | 12/2006 | Hoheisel | B33Y 80/00 378/154 |
| 7,260,171 | B1 * | 8/2007 | Arenson | A61B 6/06 378/19 |
| 7,260,174 | B2 * | 8/2007 | Hoffman | A61B 6/4241 378/207 |
| 7,284,905 | B2 * | 10/2007 | Kühn | A61B 6/032 378/119 |
| 7,366,279 | B2 * | 4/2008 | Edie | A61B 6/5282 378/7 |
| 7,734,017 | B2 * | 6/2010 | Zeitler | G01T 1/1644 378/154 |
| 8,262,288 | B2 * | 9/2012 | Shaughnessy | A61B 6/585 378/207 |
| 9,219,178 | B2 * | 12/2015 | Zhang | A61B 6/06 |
| 9,480,444 | B2 * | 11/2016 | Kappler | A61B 6/032 |
| 9,601,223 | B2 * | 3/2017 | Deych | G21K 1/025 |
| 9,615,808 | B2 * | 4/2017 | Mentrup | A61B 6/4291 |
| 10,222,489 | B2 * | 3/2019 | Fu | G01T 1/366 |
| 10,433,811 | B2 * | 10/2019 | Jacob | G01N 23/046 |
| 10,588,583 | B2 * | 3/2020 | Ergler | A61B 6/4208 |
| 10,610,191 | B2 * | 4/2020 | Sjolin | A61B 6/06 |
| 10,631,815 | B2 * | 4/2020 | Rui | G01N 23/046 |
| 10,646,176 | B2 * | 5/2020 | Hoffman | A61B 6/4241 |
| 10,779,778 | B2 * | 9/2020 | Rui | A61B 6/06 |
| 10,869,641 | B2 * | 12/2020 | Ergler | G21K 1/025 |
| 10,898,159 | B2 * | 1/2021 | Edie | G01N 23/046 |
| 11,000,242 | B1 * | 5/2021 | Nose | A61B 6/4208 |
| 11,045,153 | B2 * | 6/2021 | Takahashi | A61B 6/03 |
| 11,207,037 | B2 * | 12/2021 | Kawata | A61B 6/587 |
| 11,232,881 | B2 * | 1/2022 | Thran | G21K 1/025 |
| 2004/0131158 | A1 | 7/2004 | Hoheisel et al. | |
| 2013/0121475 | A1 | 5/2013 | Deych et al. | |
| 2015/0342554 | A1 | 12/2015 | Mentrup et al. | |
| 2018/0317869 | A1 | 11/2018 | Rui et al. | |

\* cited by examiner

PHOTON COUNTING DETECTOR BASED EDGE REFERENCE DETECTOR DESIGN AND CALIBRATION METHOD FOR SMALL PIXELATED PHOTON COUNTING CT APPARATUS

TECHNICAL FIELD

The disclosure relates to a radiation detection apparatus used in medical imaging.

BACKGROUND

For a typical scintillator detector-based conventional computed tomography (CT) system imaging, the X-ray tube emits certain amount of photons during an exposure to the scanning object, and a detector array on the other side of the scanning object measures the transmitted photons, and then the measurement is normalized to an air scan at the same scan setting without the scanning object to estimate the attenuation of the path length. Therefore, the air scan and the object scan are taken place at a different time, so any variation in the incident X-ray beam in the time domain needs to be calibrated for accurate measurement that leads to good image quality.

To achieve a good calibration of the X-ray tube flux variation over time, typically a scintillator-based energy integrating detector (EID) is installed next to the beam exit to monitor the real time X-ray tube flux change, and used as a normalization factor between scans. However, other than the X-ray tube flux change, the focal spot (FS) position also drifts more or less, depending on the tube type, over time due to the internal electrical steering variation and anode thermal expansion, as well as other design tolerances. Such positional variation usually would cause a random anti-scatter-grid (ASG) shadow profile change on the individual detector pixels, and changing the measured intensity from time to time. Such FS positional variation combined with non-ideal ASG angular alignment can cause different intensity drifts across the detector pixels, and result in ring artifacts in the reconstructed image. On the other hand, the ASG may also experience certain deformation due to high rotation speed, and cause positional and rotational speed dependent intensity variation across the pixels.

There could be different ways to overcome these issues: 1) one way is to leave a certain inactive detector area in each pixel to allow such ASG shadow variation either due to the FS movement (right) or the ASG plate deflection (left) without affecting the intensity measurement (see FIG. 1A and FIG. 1B) 2) or improve the ASG alignment accuracy to allow a good cancelation from pixel to pixel (e.g. intensity increase or decrease by the same amount) (see FIG. 2).

FIG. 1A and FIG. 1B show a type of detector design with inactive area at each pixel edge to prevent intensity shift caused by ASG angular deflection or FS movement, respectively. However, as a compromise, this approach also decreases the geometric detection efficiency.

FIG. 2 shows a detector pixel design without inactive areas. It illustrates how the ASG shadow changes with FS movement, and the intensity variation across detector pixels with different ASG plate tilting angles with respect to the nominal angles.

The dash lines indicate the nominal focusing angle for the individual ASG plates. The solid lines indicate the projected shadow boundaries with two different FS positions along the channel direction. The measured intensities of pixel 1 and 2 will decrease when FS moves from position 0 to position 1, but the intensity of pixel 4 will increase as the shadow area changes in the opposite direction, and pixel 3 remains the same.

Without a proper correction, these intensity variations across pixels would cause different normalization error for the individual pixel when the air scan and the object scan are taken with different FS locations, hence, generating ring artifact in the image.

For a semiconductor (CdTe/CZT)-based photon counting CT (PCCT), the typical detector array design usually has a much smaller pixel size compared to the conventional CT detector, due to the trade-off between charging sharing effect and the pulse pile up effect to achieve the best energy resolving performance. Typically, the pixel pitch is chosen between 250 μm and 500 μm in one dimension, compared to ~1 mm for the conventional pixel pitch. Thus, the conventional detector pixel area is usually equivalent to a N×N group of sub-pixels in PCCT, where N can be between 2 to 4. To maintain high dose efficiency, the ASG design usually still remains in the same pitch/spacing as the conventional system pixel pitch (see FIG. 3).

One important application for the PCCT is spectral imaging. To achieve good performance, accurate tube spectrum information is needed to solve the material decomposition problem. Current EID reference detectors at the tube side only monitor the total tube flux and may not be sensitive to the spectrum change over time as the tube performance changes. Therefore, new reference detector design is also needed for the incident spectrum monitoring/calibration purpose.

For a small pixelated photon counting detector (PCD) design, the ASG plates usually keep the same spacing as the conventional CT design as illustrated in FIG. 3. A 3×3 sub-pixel scheme is used as an example, for which each sub-pixel is ⅓~⅑ of the conventional detector pixel size.

In such a design, the ASG shadow now only affects sub-pixel 1 and 3 in each group, and the middle sub-pixel 2 is not affected by those effects as previously described. Therefore, even with a perfect ASG plate alignment, the sub-pixel readout would always have normalization error across the detector along the FS movement direction, and this is a random correction factor that no existing apparatus can resolve. This would generate ring artifact in the high resolution images which use the sub-pixel level readout for image reconstruction.

In reality, the ASG plates always have certain mechanical tolerances for both positional accuracy and angular accuracy. Therefore, the combined readout (e.g., 3×3 summing mode) would also encounter the same problem as described in FIG. 2, and generate ring artifact in the standard resolution images which use the combined pixel readout for reconstruction when this effect is significant enough.

In a PCCT project measurement, one typically measures 2-6 energy bin counts. As an example, for detector pixel i, the measured 5 bin counts can be modeled as the following:

$$N_{bi}(b=1,\ldots,5) = \int_{T_b}^{T_{b+1}} \Phi_b(E') \int_{E_{min}}^{E_{max}} N_{0i} S_{0i}(E) D(E, E') e^{-\sum_{j=1}^{J} \mu_j(E) l_j} dE dE'$$

$$\Phi_b(E) = \begin{cases} 1, & T_b \le E \le T_{b+1} \\ 0, & \text{others} \end{cases}$$

$N_{0i}$ is the incident flux determined by using the air scan without the scanning object. Any tube flux variation can be captured and corrected by the tube side reference detector. But the air scan flux variation can be also due to the focal spot related movement as previously explained, and this cannot be captured by the reference detector readout (Ref) at the tube side, therefore introduces error in using this forward model to estimate the material path lengths:

$$\frac{N_{bi}\_\text{ref}}{N_{0i}\_\text{ref}} = \int_{T_b}^{T_{b+1}} \Phi_b(E') \int_{Emin}^{Emax} S_{0i}(E) D(E, E') e^{\sum_{j=1}^{J} \mu_j(E) l_j} dE dE'$$

$$N_{bi}\_\text{ref} = \frac{N_{bi}}{\text{Ref}_{obj}}$$

$$N_{0i}\_\text{ref} = \frac{N_{0i}}{\text{Ref}_{air}}$$

$N_{bi}$_ref is the reference reading corrected bin count measurement with scanning object, and $N_{0i}$_ref is the reference reading corrected air scan. $\text{Ref}_{obj/air}$ is the reference detector reading for the object/air scan. The reference detector reading at the tube side is not sensitive to the focal spot movement related flux change on the main detector.

In addition, the above forward model requires accurate incident spectrum $S_{0i}(E)$ as a known input, and any drift of this spectrum over time without knowing also introduces error in the estimated path lengths and generates bias in the reconstructed image.

SUMMARY

In order to monitor the FS movement-induced ASG shadow shift, and correct the associated detector pixel intensity variation, a new PCD-based edge reference detector design with an extended ASG covered on top of the edge detector pixels is presented herein (FIG. 4).

The edge reference detectors need to be in the fan beam coverage but outside the scan field of view (FOV) so that the measurement is not affected by the change of scanning path length. The edge reference detector comprises at least one group of sub-pixels with a N×N pattern, where N>=3. Therefore, the middle pixel(s) are not affected by the ASG shadow effect.

The signal variations of the edge reference detector pixels under the ASG shadow are used to estimate the real-time FS movement, which is used to estimate the shadow/signal variation on the main detector pixels that are in the scan FOV.

Depending on the FS movement speed, the estimated variation is corrected on each view, or on a group of views. The correction is applied on both the sub-pixel level readout and the combined-pixel mode readout.

With a two dimensional (2D) ASG design on the main detector, one can apply this correction on both the channel direction and the row direction FS movement.

Using the PCD, the edge reference detector described herein also has multiple energy bin measurements to monitor the tube spectrum variation.

BRIEF DESCRIPTION OF THE DRAWINGS

The application will be better understood in light of the description which is given in a non-limiting manner, accompanied by the attached drawings in which.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

Figure 5:
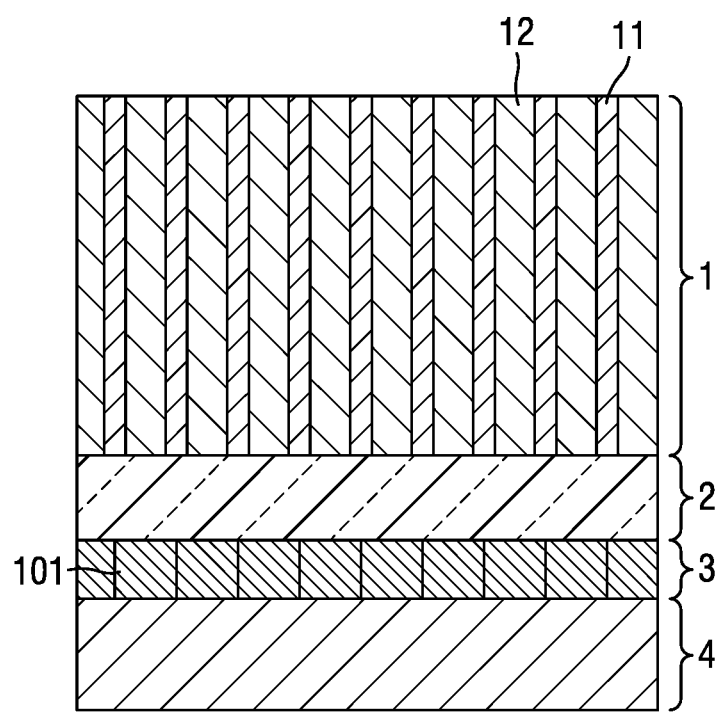
FIG. 5 shows a cross section of scintillator-based EID.

A scintillator-based EID is shown in FIG. 5. It comprises a grid 1 that includes radiation-absorptive (e.g., Pb) members 11 and radiation-transmissive (e.g., Al) members 12 alternatively arranged in the form of slits or a matrix. The members can be one-dimensional (1D) or 2D. The grid 1 is positioned on substrate 2 and photoelectric conversion unit 3 having pixels 101, which is arranged on scintillator 4.

Figure 4:
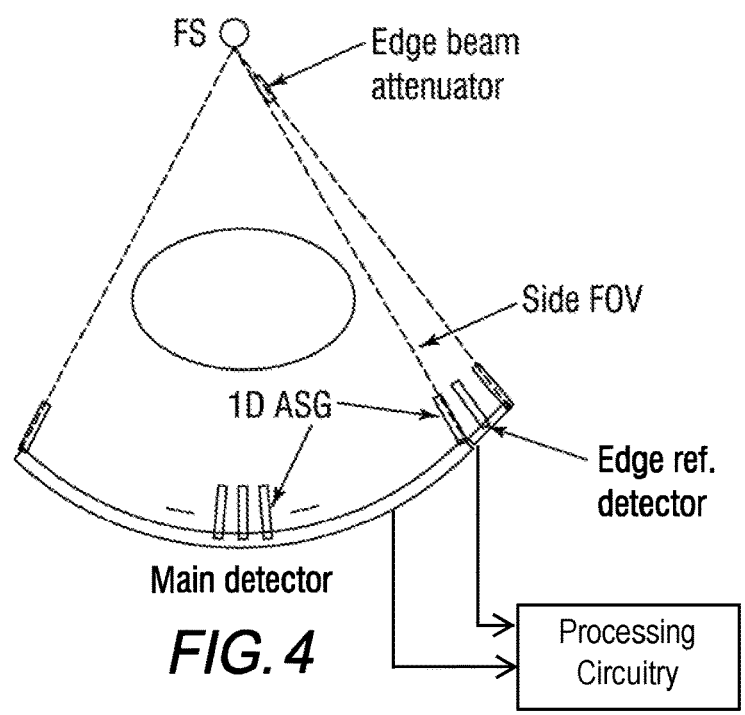
FIG. 4 shows a schematic of an edge reference detector design.

A PCD-based edge reference detector design with an edge ASG covering the top of the edge detector pixels is shown in FIG. 4.

In one embodiment, as shown in FIG. 4, a small section of the PCD pixels are located at the edge of the main PCD array. A small portion of the ASG, same as, or different from the ASG on the main detector are mounted on those edge PCD pixels using a N×N (N>=3) pixel group pitch, focusing to the FS. To avoid pileup effect which will skew the flux measurement, a piece of beam attenuator with appropriate attenuation length is added at the beam exit to make sure the measurement of the reference detector is at low flux condition. The beam attenuator may be made of common attenuation materials like Al, Cu, Ti, etc. This can be a part of or an extension of the bowtie filter that shapes the beam profile on the main detector.

As shown in FIG. 4, the PCD based edge reference detector is located outside the scan FOV to provide real-time monitoring of the FS movement as well as the tube spectrum variation. An extension of the main detector ASG or a different ASG is needed to cover the edge reference detector. As an alternative, different ASG patterns can be used on different sections of the detector to monitor the FS movement in both the channel and row direction if a 2D ASG is used for the main detector.

Figure 6:
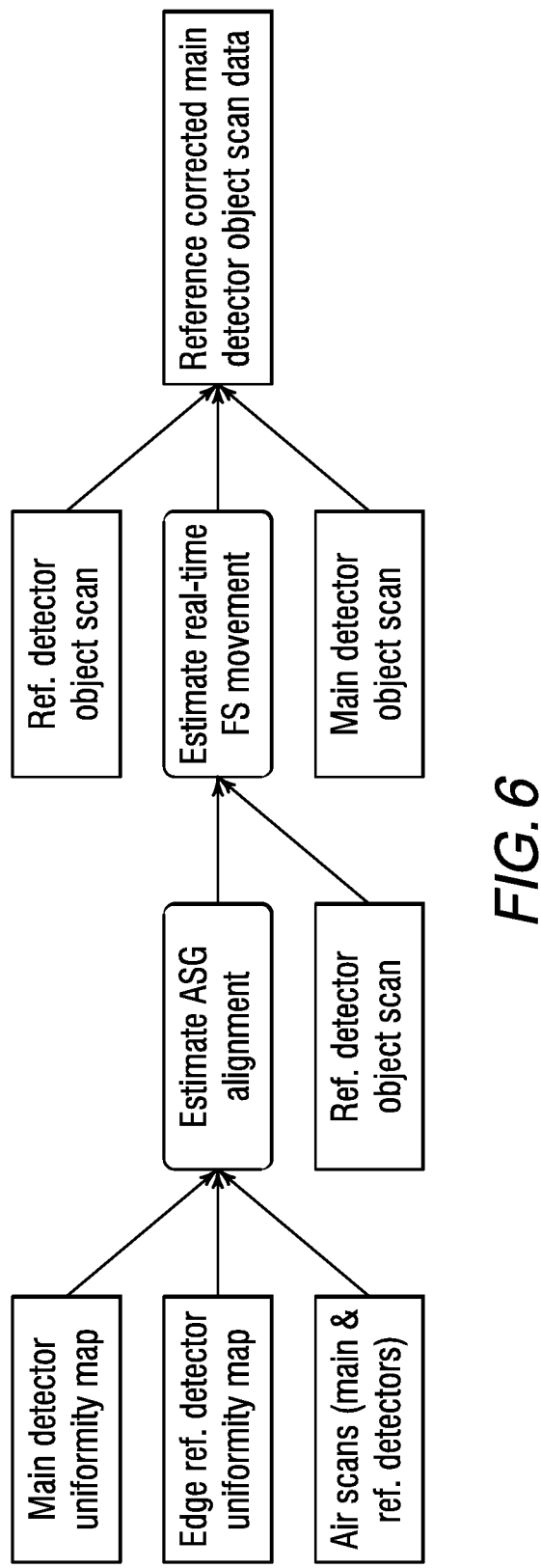
FIG. 6 shows a schematic of edge reference detector correction workflow.

FIG. 6 shows the main workflow of the edge reference detector correction.

During scans, the edge reference detector will always readout simultaneously with the main detector, and used for data processing. No ASG scans would be needed to measure the pixel uniformity map for both the main detector and the edge reference detector, and used as normalization factors for the individual pixels to estimate the ASG alignment. Then, the intensity (e.g. total counts) variation over the scan can be used to estimate the ASG shadow change, then using the geometric information to estimate the FS movement along the orthogonal direction of the ASG plate orientation.

For the pixels (central ones) that are not under the ASG shadow influence, the signal change can be used to monitor the tube flux variation over time, similar to the conventional EID reference detector at the tube side. They can also monitor the tube spectrum variation with multiple energy bin measurements. With the estimated FS movement, the corresponding intensity drifts between the air scan and the object scan on the main detector pixels can be estimated and corrected.

In order to estimate the FS movements from the edge reference PCD, various designs may be selected.

Figure 7B:
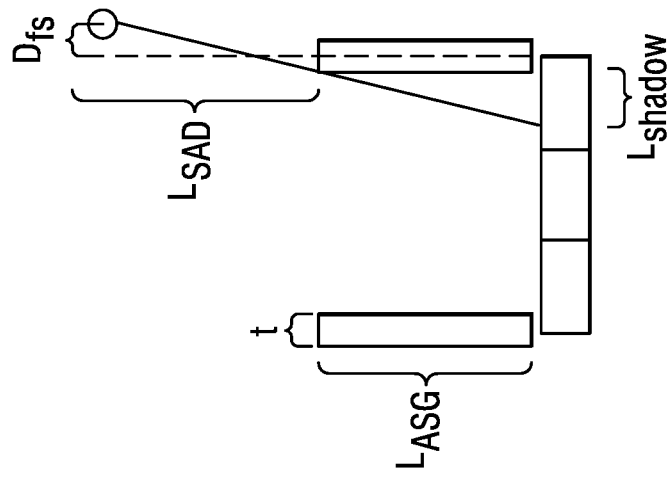
FIG. 7B shows a schematic of shadow caused by FS movement in channel direction with a 1D ASG with higher plates. The shadow is bigger compared to the design in FIG. 7A with the same FS movement.
Figure 7A:
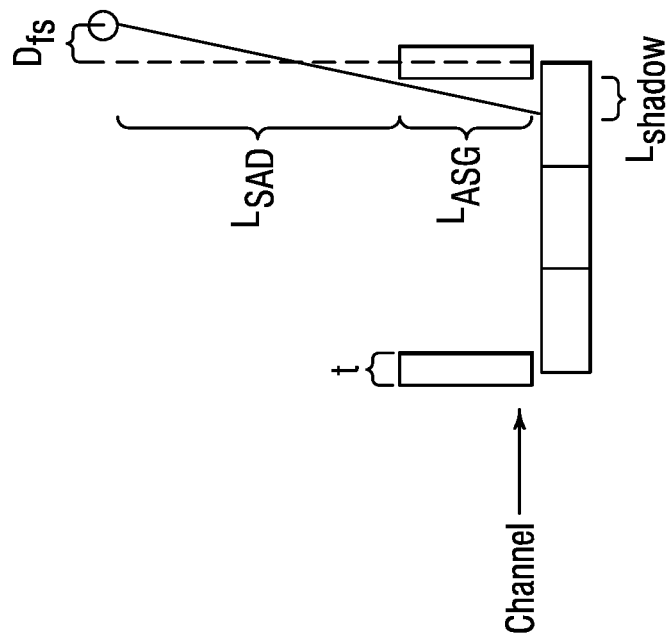
FIG. 7A shows a schematic of shadow caused by FS movement in channel direction with a 1D ASG.

In one embodiment, the same ASG design (height, thickness and spacing) as the one on the main detector is used (FIG. 7A).

In another embodiment, a higher ASG plate with the same thickness and spacing as the main ASG is used to enhance the measurement sensitivity to the FS movement (FIG. 7B). The estimated FS drift $D_{fs}$ in the channel direction is approximated as:

$$D_{fs} = L_{shadow} * \frac{L_{SAD}}{L_{ASG}}, \text{ with } L_{SAD} \gg L_{ASG} \gg t; \quad \text{(Eq. 1)}$$

In one embodiment, processing circuitry 40, such as, e.g., a CPU executing a stored program, is configured to calculate $D_{fs}$ using Equation 1. See FIGS. 4 and 6. Therefore, with larger $L_{ASG}$, the shadow caused pixel intensity change is more significant and gives more accurate FS movement estimate with the same measurement statistics.

The same concept also applies for a 2D ASG design, and the FS movement in the row direction can also be estimated using the same formula when a 1D ASG along the other direction is used, see Eq. 1.

The measured intensity, in this case, the total counts of the edge reference detector pixels are used to estimate $L_{shadow}$. Using a 1D ASG design as an example, one method is based on the linear approximation ignoring the charge sharing/cross talk effect between neighbouring pixels: $N \approx N_0 (L_{pixel} \times x_{asg} - L_{shadow})/(L_{pixel} - x_{asg})$, where $L_{pixel}$ is the pixel size, $x_{asg}$ is the initial ASG shadow which is t/2 with ideal ASG-pixel alignment, and $L_{shadow}$ is the additional shadow caused by non-ideal FS-ASG alignment, and in this case, by FS movement.

Figure 2:
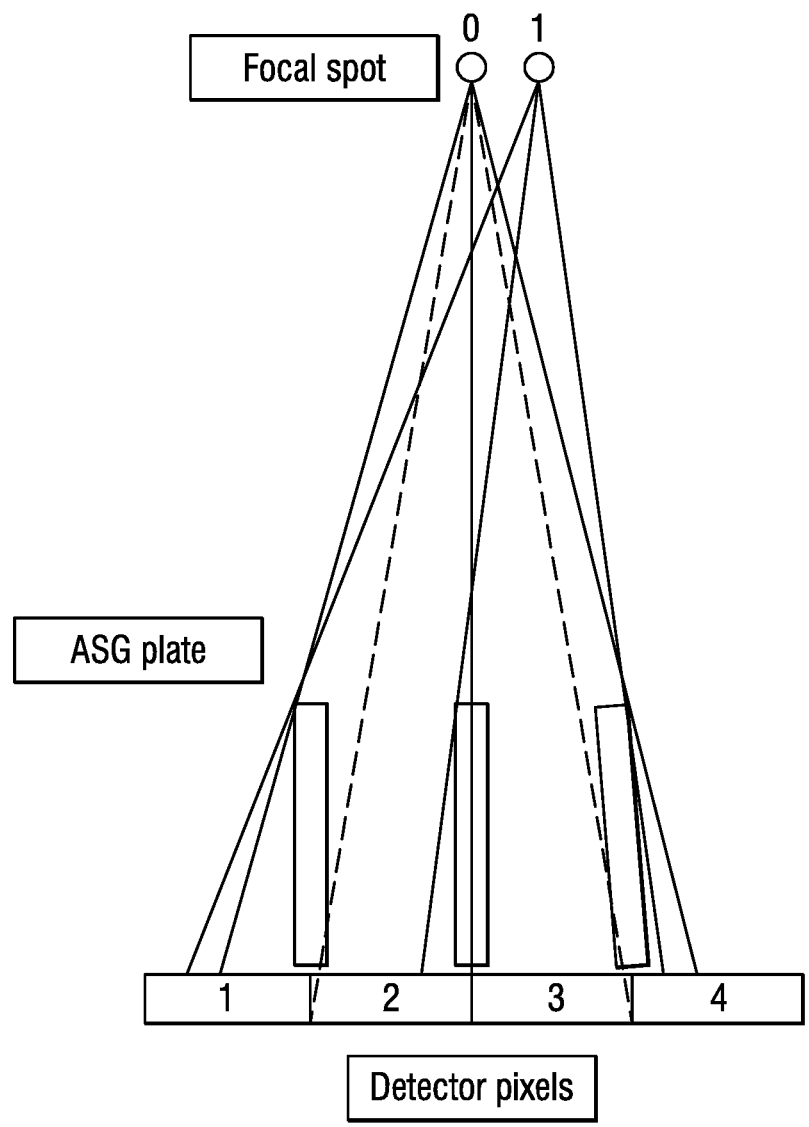
FIG. 2 shows a schematic of a detector pixel design without an inactive area.
Figure 3:
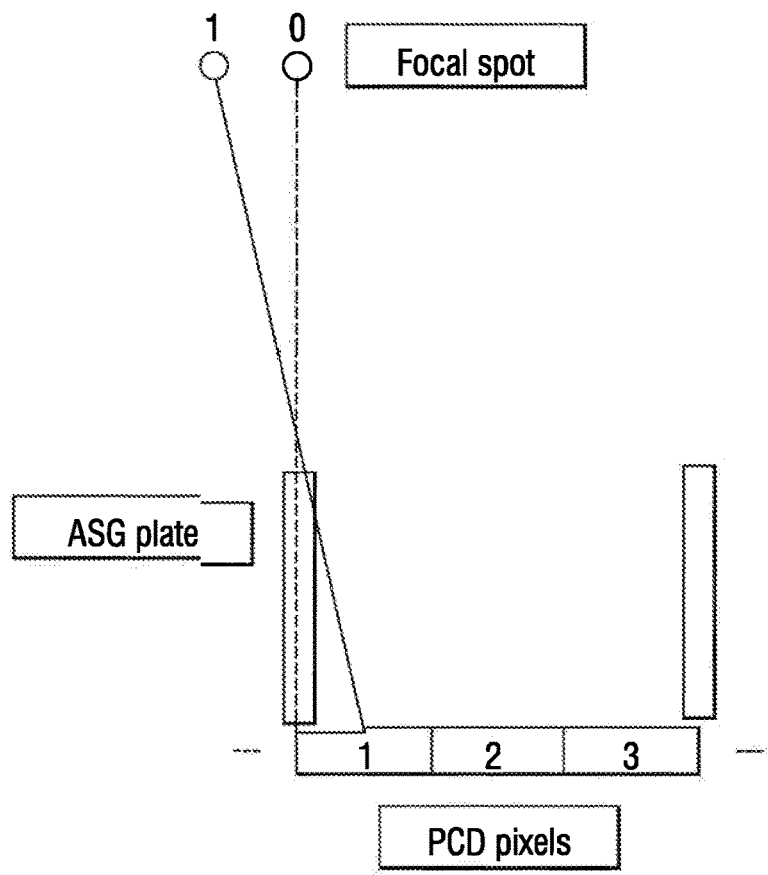
FIG. 3 shows an example of ASG design with a small pixelated PCD.
Figure 8:
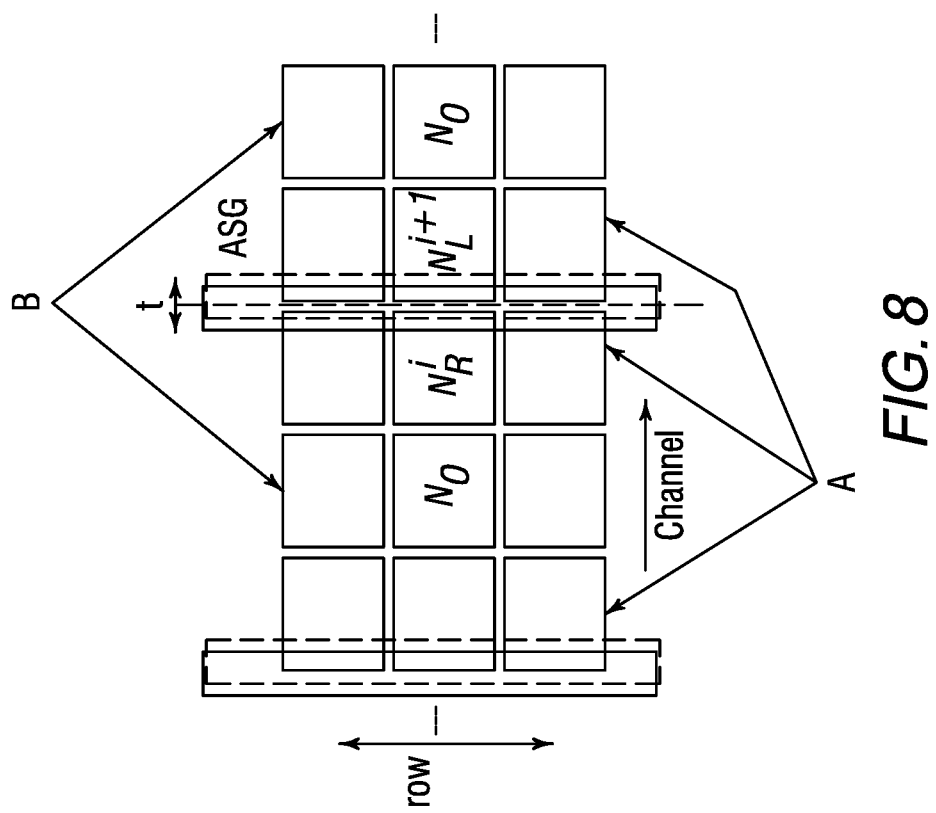
FIG. 8 shows a schematic of an edge reference detector covered by 1D ASGs.

In reality, $x_{asg}$ can deviate from t/2 due to ASG alignment tolerance (FIG. 2), as well the deflection under gantry rotation, and one can estimate the initial shadow $x_{asg}$ based on the pixel intensity difference between neighboring pixels after normalizing with the no ASG measurements (detector uniformity map). One method is to compare the normalized intensity of the ASG covered pixels with the uncovered ones to estimate $x_{asg}$ $$\frac{N_{ASG}}{N_0} = 1 - x_{asg}/L_{pixel}, \quad \text{(Eq. 2)}$$

where $N_{ASG}$ is the normalized ASG covered pixel intensity, and $N_0$ is the normalized uncovered pixel intensity. $x_{asg}$ is rotation speed dependent, and this measurement needs to be taken for every available rotation speed for correction, see FIG. 8 for a demonstration for the 1D ASG populated at channel direction. The ASG covered pixels are marked as A, and the uncovered ones are marked as B. The dashed boxes indicate the misalignment of ASG from its ideal location (solid boxes).

A variation of the method to minimize the effect from ASG alignment tolerance and estimate the shadow is to use the sum of two neighboring edge pixels that are under the ASG septa, assuming the charge sharing/cross talk effect is 0 between these two pixels:

$$(N_R^i + N_L^{i+1}) = 2N_0(2L_{pixel} - t - L_{shadow})/(2L_{pixel}) \quad \text{(Eq. 3)}$$

A variation of the method can further include the charge sharing/cross talk effect between the neighboring pixels assuming the charge sharing/cross talk effect is proportional to the boundary length between the pixels to further improve the estimation accuracy.

The new reference normalized air scan and object scans are given by:

$$N_{0i}\_\text{ref} = \frac{N_{0i}}{Ref_{air}} * f_{0i}\_\text{shadow}, \quad \text{(Eq. 4)}$$

$$N_{bi}\_\text{ref} = \frac{N_{bi}}{Ref_{obj}} * f_i\_\text{shadow}$$

Where, $f_{i}\_\text{shadow}$ is the additional shadow correction factor for the main detector pixel i based on the estimated FS drift $D_{fs}$ from the edge reference detector measurement. An alignment factor $m_i$ is added to account for the initial orientation of the ASG plates with respect to the FS position, and is either 0 or 1 (see FIG. 9). $m_i$ can be determined by comparing the detector intensity variations between a series of air scans that cover the full FS position range.

$$f_{i_{shadow}} = \frac{L_{main} - m_i * D_{fs} * \frac{L_{ASG(main)}}{L_{SAD(main)}}}{L_{main}} \quad \text{(Eq. 5)}$$

Figure 9:
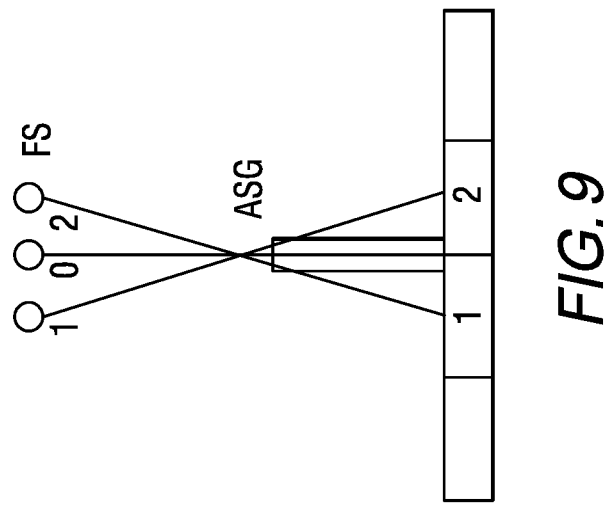
FIG. 9 shows a schematic showing the ASG shadow influence on two neighboring pixels with non-ideal ASG-FS alignment.

With reference to FIG. 9, the ASG shadow influences on two neighboring pixels with non-ideal ASG-FS alignment. $m_1=0$, $m_2=1$ when FS position is between 0 and 1; $m_1=1$, $m_2=0$ when FS position is between 0 and 2. Due to the ASG plates alignment variations, the 0 position could be different for the pixels under ASG, and can be estimated through a few air scans that cover the full FS movement range.

This correction can be applied on different rotation speed, as an additional correction to the air normalization which includes the ASG deflection variation on the main detector at different rotation speed.

In order to make sure that the edge reference PCD is at low flux region to avoid complications due to pulse pileup, one can employ multiple beam attenuator designs with different attenuation lengths to cover the full operational flux range.

When a mA/kV setting is selected for the scan, the optimal beam attenuator is pre-selected and put in position for those edge reference PCDs to make sure the measurement satisfies the low flux condition with sufficient statistics for an accurate estimation.

The low flux condition can be defined as $n\tau<0.05$, where n is the pixel count rate, and $\tau$ is the ASIC dead time for processing one signal pulse. The appropriate length of the attenuator can be theoretically calculated and designed based on the material's attenuation coefficient and the simulated tube spectrum.

Figure 10A:
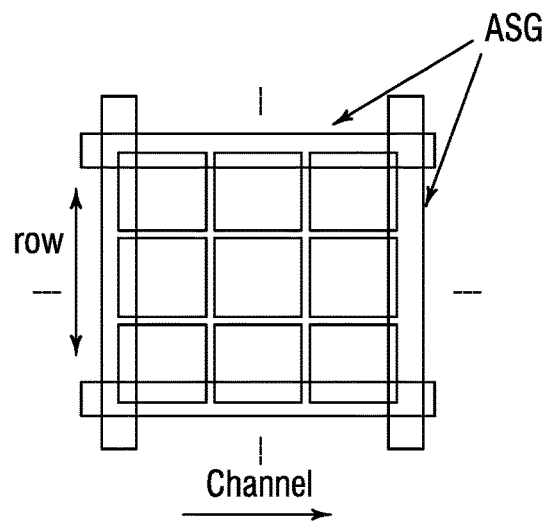
FIG. 10A shows a schematic of a main detector with a 2D ASG.
Figure 10B:
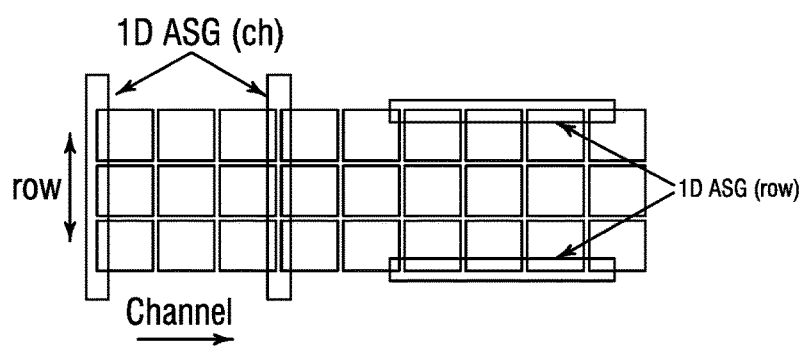
FIG. 10B shows a schematic of an edge reference detector with two 1D ASGs.

If a 2D ASG design is used on the main detector (FIG. 10A), the edge reference detector can use two 1D ASGs, one on the channel direction and the other on the row direction at different locations, to estimate the FS movement on each direction separately (FIG. 10B).

A variation of the design for 2D ASG on the main detector is to use the same or a different 2D ASG design on the edge reference detector as well.

Figure 11:
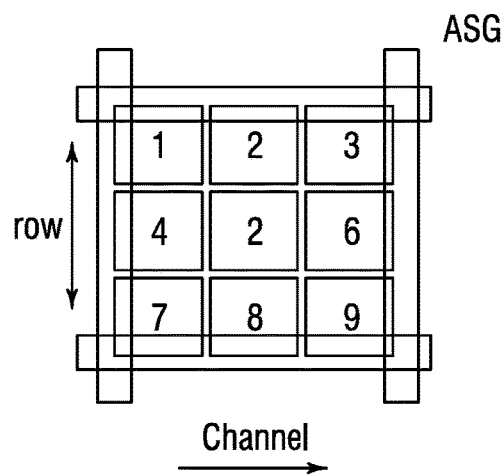
FIG. 11 shows a schematic of an edge reference detector with a 2D ASG.
Figure 12:
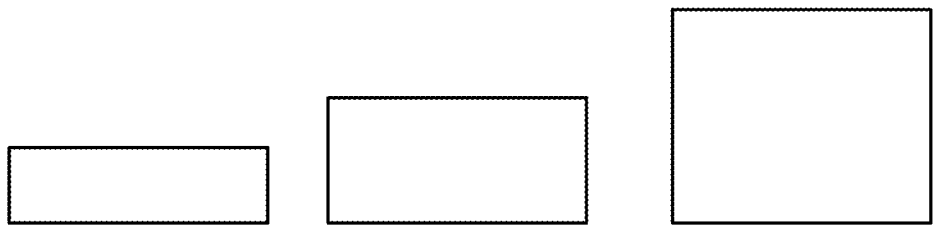
FIG. 12 shows an illustration of multiple edge beam attenuators with different attenuation lengths.

In an example of a 3×3 sub-pixel group for the edge detector (FIG. 11), pixels 2 and 8 are only under the row direction ASG shadow while pixel 4 and 6 are only under the channel direction ASG, therefore, they can be used respectively to estimate the FS movement on both directions.

In conventional CT systems, the reference detectors are typically scintillator-based energy integrating detectors, and located at the tube side. The PCD based edge reference detector design described herein can provide the FS position information as well as the tube spectrum information, which are crucial for a small pixelated PCCT measurement and the resulted image.

Figure 1A:
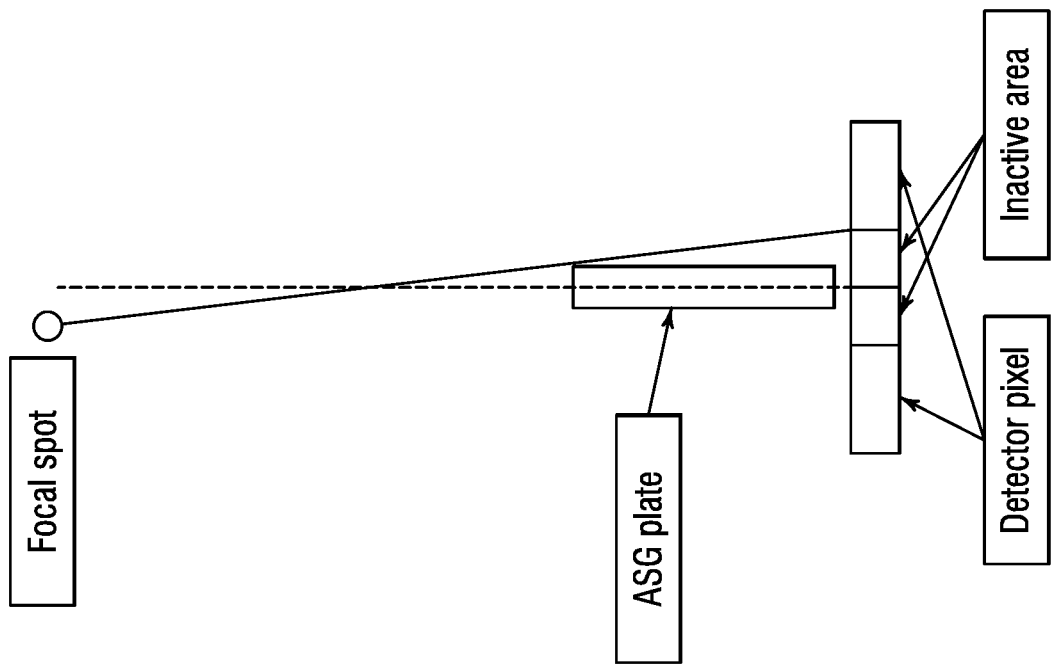
FIG. 1A shows a schematic of a detector design with an inactive area at each pixel to prevent intensity shift caused by ASG angular deflection.
Figure 1B:
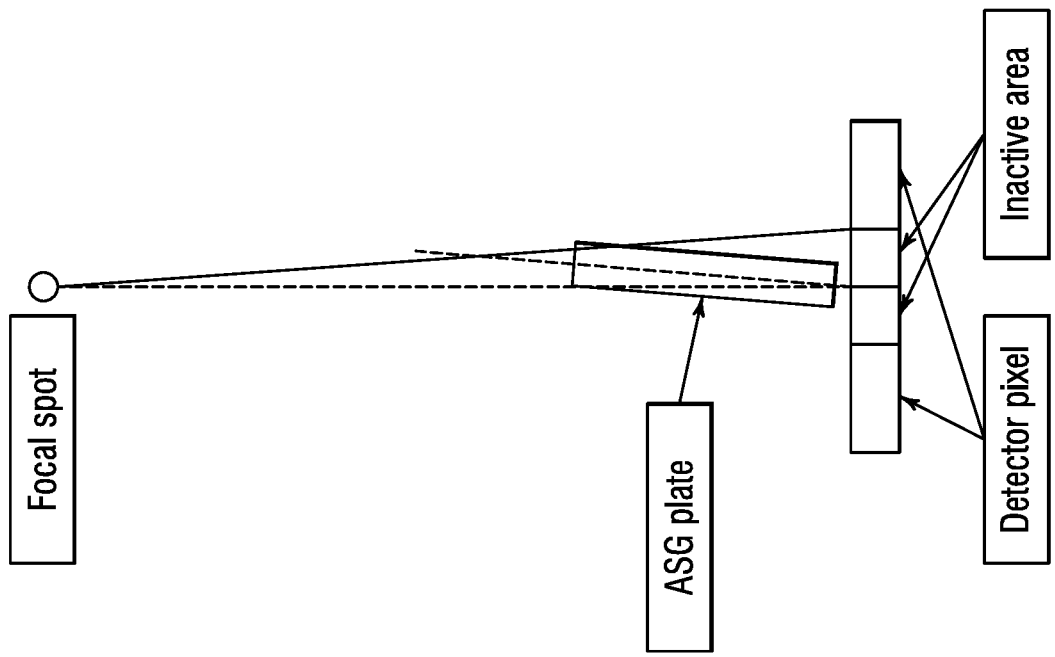
FIG. 1B shows a schematic of a detector design with an inactive area at each pixel to prevent intensity shift caused by FS movement.

In the design in FIG. 1A and FIG. 1B, as the inactive area is introduced for every pixel, the dose efficiency is compromised, compared to the design described herein.

Obviously, numerous modifications and variations of the embodiments presented herein are possible in light of the above teachings. It is therefore to be understood that within the scope of the claims, the disclosure may be practiced otherwise than as specifically described herein.

The invention claimed is:

1. A photon counting CT apparatus, comprising:
a photon counting detector (PCD) arranged in a two-dimensional (2D) array of pixels;
an anti-scatter-grid (ASG) arranged associated with the PCD and configured to remove scattered radiation, wherein the PCD comprises a main detector positioned within a scan field of view (FOV) of a fan beam coverage and a reference detector positioned outside the FOV; and
processing circuitry configured to determine a movement of a focal spot of an X-ray tube based on a count detected by the reference detector,
wherein the processing circuitry is further configured to estimate a variation in an amount of incidence on the PCD based on a count detected by the reference detector.

2. The photon counting CT apparatus of claim 1, wherein the reference detector comprises a plurality of pixels, and
wherein the processing circuitry is further configured to determine the movement of the focal spot based on, among counts detected at the plurality of pixels, a first count detected at a first pixel of the plurality of pixels, which is influenced by a shadow of the ASG, and a second count detected at a second pixel of the plurality of pixels which is not influenced by the shadow of the ASG.

3. The photon counting CT apparatus of claim 2, wherein the processing circuitry is further configured to determine a length of the shadow of the ASG based on the first count and the second count, and determine the movement of the focal spot based on the length of the shadow of the ASG.

4. The photon counting CT apparatus of claim 3, wherein
the length of the shadow of the ASG is a first length indicating a variation in the length of the shadow of the ASG created by the ASG upon the movement of the focal spot of the X-ray tube from a first position to a second position, and
the processing circuitry is further configured to determine the first length based on the first count, the second count, and a second length, wherein the second length is a length of a shadow created by the ASG when the focal spot is positioned at the first position.

5. The photon counting CT apparatus of claim 3, wherein the processing circuitry is further configured to determine the movement of the focal spot based on the length of the shadow of the ASG and a height of the ASG covering the reference detector.

6. The photon counting CT apparatus of claim 1, wherein the processing circuitry is further configured to correct, based on the movement of the focal spot of the X-ray tube, a count detected by the main detector.

7. The photon counting CT apparatus of claim 6, wherein the processing circuitry is further configured to correct a count detected based on the movement of the focal spot in a channel direction and a count detected based on the movement of the focal spot in a row direction, each detected by the main detector.

8. The photon counting CT apparatus of claim 1, wherein the processing circuitry is further configured to correct the amount of incidence on the PCD based on the estimated variation in the amount of incidence.

9. The photon counting CT apparatus of claim 1, wherein the reference detector comprises an edge reference PCD positioned outside the FOV, but within a fan beam coverage of the X-ray tube.

10. A photon counting CT apparatus comprising:
a photon counting detector (PCD) arranged in a two-dimensional (2D) array of pixels; and
an anti-scatter-grid (ASG) arranged associated with the PCD and configured to remove scattered radiation,
wherein the PCD comprises a main detector positioned within a field of view (FOV) and a reference detector positioned outside the FOV, and the reference detector comprises at least one group of pixels with an N×N pattern, where N≥3.

11. A photon counting CT apparatus comprising:
a photon counting detector (PCD) arranged in a two-dimensional (2D) array of pixels; and
an anti-scatter-grid (ASG) arranged associated with the PCD and configured to remove scattered radiation,
wherein the PCD comprises a main detector positioned within a field of view (FOV) and a reference detector positioned outside the FOV, and the ASG comprises a first ASG covering the main detector and a second ASG covering the reference detector, and the second ASG has a height greater than a height of the first ASG.

12. The photon counting CT apparatus of claim 11, wherein the first ASG comprises a two-dimensional ASG, and the second ASG comprises two one-dimensional ASGs, one of the two one-dimensional ASGs on a channel direction and the other of the two one-dimensional ASGs on a row direction.

13. A photon counting CT apparatus comprising:

a photon counting detector (PCD) arranged in a two-dimensional (2D) array of pixels; and an anti-scatter-grid (ASG) arranged associated with the PCD and configured to remove scattered radiation, wherein the PCD comprises a main detector positioned within a field of view (FOV) and a reference detector positioned outside the FOV, and multiple beam attenuators with different attenuation lengths provided between an X-ray tube and the reference detector.

14. A method performed by a photon counting CT apparatus, the photon counting CT apparatus comprising: a photon counting detector (PCD) arranged in a two-dimensional (2D) array of pixels, and comprising a main detector positioned within a field of view (FOV) and a reference detector including a plurality of pixels positioned outside the FOV; and an anti-scatter-grid (ASG) arranged associated with the photon counting detector and configured to remove scattered radiation, the method comprising:

determining a length of a shadow created by the ASG based on, among counts detected at the plurality of pixels included in the reference detector, a first count detected at a first pixel of the plurality of pixels, which is influenced by a shadow of the ASG, and a second count detected at a second pixel of the plurality of pixels which is not influenced by the shadow of the ASG; and determining a movement of a focal spot of an X-ray tube based on the length of the shadow of the ASG.

15. The method of claim 14, wherein the determining the length of the shadow created by the ASG comprises detecting the counts at the plurality of pixels included in an edge reference PCD in the reference detector positioned outside the FOV, but within a fan beam coverage.

16. The method of claim 14, wherein the determining the length of the shadow created by the ASG comprises detecting the counts at the plurality of pixels included in the reference detector at at least one group of pixels with an N×N pattern, where N≥3.

* * * * *